United States Patent [19]
Guglielmotti et al.

[11] Patent Number: 6,020,356
[45] Date of Patent: Feb. 1, 2000

[54] PHARMACEUTICAL COMPOSITION FOR THE TREATMENT OF AUTOIMMUNE DISEASES

[75] Inventors: Angelo Guglielmotti; Paolo Dionisio, both of Rome, Italy

[73] Assignee: Angelini Ricerche S.p.A. Societa' Consortile, Pomezia, Italy

[21] Appl. No.: 09/068,011
[22] PCT Filed: Oct. 26, 1996
[86] PCT No.: PCT/EP96/04672
   § 371 Date: Sep. 3, 1998
   § 102(e) Date: Sep. 3, 1998
[87] PCT Pub. No.: WO97/16185
   PCT Pub. Date: May 9, 1997

[30]    Foreign Application Priority Data

Oct. 31, 1995  [IT]  Italy .................................. MI95A2242

[51] Int. Cl.[7] .......................... A61K 31/56; A61K 31/415
[52] U.S. Cl. .......................... 514/403; 514/171; 514/177; 514/406
[58] Field of Search ..................................... 514/171, 177, 514/403, 406

Primary Examiner—Theodore J. Criares
Attorney, Agent, or Firm—Oblon, Spivak, McClelland, Maier & Neustadt, P.C.

[57]    ABSTRACT

A pharmaceutical composition comprising an anti-inflammatory drug capable of suppressing the production of cytokines (CSAID) an immunosuppressant and a pharmaceutically acceptable excipient.

8 Claims, No Drawings

PHARMACEUTICAL COMPOSITION FOR THE TREATMENT OF AUTOIMMUNE DISEASES

This application is a 371 of PCT/EP96/04672 filed Oct. 26, 1996, and claims the benefit of Italian application MI 95A002242 filed Oct. 31, 1995.

The present invention relates to a pharmaceutical composition comprising an 2-((1-benayl-indazol-3-yl)-methoxy)-2-methyl propionic acid (bindarit), an immunosuppressant and a pharmaceutically acceptable excipient.

It is known that the autoimmune diseases form a wide group of pathologies characterized by inflammatory phenomena and destruction of tissues caused by the production, by the immune system, of body's own antibodies. Examples of diseases considered to be autoimmune in nature are: rheumatoid arthritis, glomerulonephritis, Hashimoto's thyroiditis, systemic lupus erythematosus, myasthenia gravis, autoimmune hemolytic anemia, autoimmune thrombocytopenic purpura, autoimmune disorders and type 1 diabetes.

Presently, in the autoimmune diseases therapy there are used steroidal and non-steroidal anti-inflammatory drugs, gold compounds, penicillins and immunosuppressants.

Non-steroidal anti-inflammatory drugs (NSAID) show, together with the anti-inflammatory activity, also an anti-pyretic and a non-narcotic analgesic effect. They are widly used both in the acute inflammatory therapy and in chronic inflammatory treatment. For this reason they are currently used in the treatment of autoimmune pathologies, wherein the inflammatory process is often very important. Even if other mechanisms of action may not be excluded, their activity is mainly due to the capability of inhibiting the enzymes responsible for prostaglandins (PG) and leucotriens synthesis, in particular cyclooxygenases and lipooxygenases. This mechanism of action is mostly responsible also for side effects on different organs (mainly gastrointestinal and renal) that occur as a consequence of the prolonged use of said drugs.

Further, to the mainly symptomatic effects that are obtained by the anti-inflammatory drugs in the acute phase of autoimmune pathologies, the most important therapeutical effects are obtained by non-steroidal drugs such as, for example, cyclophosphamide.

However, this kind of drug can not be administered for prolonged periods of time because of the onset of different type of side effects having considerable side effects.

In fact, that treatment must be stopped because of the onset of toxicity on organs or of systemic nature in more than 20% of patients within 12 months. The remission phases last for a very variable period of time (from 1 to 18 months on average) and, although a second and often a third therapy cycle may give positive results, more than 50% of patients that initially responded to the therapy must stop it after 3–6 years because of relapses and/or because of the late toxicity. The organs that are most frequently involved are kidneys, liver, blood and reproductive apparatus.

Therefore, toxic effects of therapies employed in autoimmune phatologies are a serious obstacle to their use and thus there is a serious need of a product capable of reducing the undesired side effects of drugs employed in said therapies, thus reducing the doses or the number of administrations.

Now, it has been unexpectatebly found that bindarit (1) allows reducing the immunosuppressants dose in the prolonged treatment of autoimmune diseases, without reducing the therapeutical efficacy thus improving the tolerability.

Therefore, it is a first object of the present invention to provide a pharmaceutical composition comprising bindarit an immunosuppressant and a pharmaceutically acceptable excipient.

Further, it is a second object of the present invention to provide a method of treating autoimmune diseases characterized by the concurrent administration bindarit and an immunosuppressant.

Typical examples of immunosuppressants according to the present invention are: cyclosporin, azatioprin, methotrexate, cyclophsphamide, FK 506, cortisol, betametasone, cortisone, desametasone, flunisolide, prednisolone, methylprednisolone, prednisone, triamcinolone, alclometasone, amcinonide desonide and desoxymetasone.

Typical examples of diseases that can benefit from the concurrent treatment with bindarit and an immunosuppressant are: rehumatoid arthritis, glomerulonephritis, Hashimoto's thyroiditis, systemic lupus erythematosus, myasthenia gravis, autoimmune hemolytic anemia, autoimmune thrombocytopenic purpura, autoimmune hepatitis, type 1 diabetes and similar.

The amount of bindarit will range depending on factors which are well known to the person skilled in the art such as, for example, the type of autoimmune disease, the severity of said disease, the body weight of the patient, the pharmaceutical dosage form, the route of administration, the number of dosage forms administred daily and the efficacy of the used compounds. However, the optimum amount may be easly determined by routine procedures of "dose-finding".

Generally, the amount of bindarit will be of from 1 to 50 mg/Kg/day. More preferably, it will be of from 4 to 35 mg/Kg/day.

Also the amount of the immunosuppressant drug will range depending on factors well known to the person skilled in the art such as, for example, the type of autoimmune disease, the severity of said disease, the body weight of the patient, the pharmaceutical dosage form, the route of administration, the number of dosage forms administred daily and the efficacy of the used compounds. However, the optimum amount may be easly determined by routine procedures particularly considering that the usual dosages of immunosuppressants are known in the literature (Goodman and Gilman 8th ed.).

Generally, the amount of the immunosuppressant drug will be such that it insures an administration level of from 0.01 to 100 mg/Kg/day.

For example, in the particular case of cyclophosphamide it will be about 30–40% lower compared to the usual one. Therefore, it will prefearably be of from 0.01 to 10 mg/Kg/day. More preferably, it will be of from 0.05 to 5 mg/Kg/day.

In its turn, in the case of prednisone, said amount will be also 30–40% lower compared to the usual one. Therefore, it will preferably be of from 0.01 to 1 mg/Kg/day. More preferably, it will be of from 0.05 to 0.5 mg/Kg/day.

Example of suitable dosage forms are tablets, capsules, coated tablets, granules, solutions and syrups for oral administration, gels, ointments, creams and medicated patches for topic administration, suppositories for rectal administration and sterile solutions for injectable, aerosolic and ophthalmic administration.

In addition to usual excipients, the compositions may comprise suitable additives for pharmaceutical use such as preservatives, stabilizers, surface active agents, emulsifiers, salts for the regulation of the osmotic pressure, buffers, flavouring agents and colouring agents.

They may also comprise liposomes, vesicles and other forms useful to obtain a controlled release of pharmacologically active compounds. Further, they can be formulated in form of stratified tablets containing layers which have a different speed of disintegration.

If particular treatments require it, the compositions of the present invention may comprise other compatible active ingredients whose concurrent administration is therapeutically useful.

The pharmaceutical compositions can be producted according to conventional techniques of the pharmaceutical chemist comprising mixing, granulating and compressing, when needed, or various mixings and dissolutions of the ingredients, depending on what is appropriate for obtaining the desired compound.

EXPERIMENTS

1. Bindarit Effects on Cytokines

Bindarit effect on the production of inflammatory cytokines has been evaluated in a mouse model wherein, after administration of concanavaline A (0.3 microg/mouse i.v.), there have been measured serum levels of interleukine-6 (IL-6) both in control animals and in animals treated with 200 mg/Kg of bindarit orally. The experiment results (Table 1) show that in the animals receiving bindarit, the IL-6 serum levels are about 40% lower compared to the untreated controls ($10.2 \pm 2.1$ vs. $16.5 \pm 6.4$ nanogram/ml; 6 animals in each group).

Bindarit capability to reduce the inflammatory cytokines production allows to count this product among CSAID drugs, being already known that bindarit is devoid immunosuppressive activity and that it is not active on cyclooxygenase and lipooxygenase (2).

2. Bindarit and Cyclohosphamide in a Mouse Model of Lupus Erythematosus.

NZB/W F1 hybrid mice spontaneously generate an autoimmune pathology which is clinically and immunologically similar to human lupus systematic erythematosus (SLE). This mouse model of SLE appears to be highly predictive and it is generally used as a preclinic model for studying new ways of treatment. Drugs conventionally used in human therapy are, in fact, active in this animal model, characterized by a substantial proteinuria, by the presence of autoantibodies and circulating immunocomplexes and by the growth of glomerulonephritis, that in these animals is the main cause of death. Immunosuppressants such as cyclophosphamide and prednisone are capable of delaying the patology progress, however their therapeutic potential is limited by their general toxicity and by the high neoplasia incidence and viral infections resulting from their use.

Bindarit, administered to NZB/W F1 female mice (26 each group) as medicated diet at 0.5%, which produces hematic levels of bindarit of from 50 to 200 micrograms/ml (determined by inverse phase HPLC), together with cyclophosphamide bola at low doses (2×22.5 and 2×45 mg/Kg ip) proved to be capable of insuring an activity comparable to that obtained at high doses of cyclophosphamide thus favouring a decrease of toxicity phenomena associated to the immunosuppressive therapy. The treatment with bindarit together with cyclophosphamide, in fact, has significantly prolonged the life of the animals (Table 2) and it has further strengthened the effects of cyclophosphamide on the immunological parameters typical of this model (Table 3) improving substantially the course of the pathology in comparison to both the control animals and the animals treated with bola of cyclophosphamide at high doses (2×90 mg/Kg ip).

These results prove that bindarit reduces the amount of immunosuppressors to be administered with consequent reduction of those toxic phenomena that often limit the use thereof in this class of pathologies.

3. Bindarit and Corticosteroides in Man.

10 patients (8 male and 2 female of from 17 to 60 years old) suffering from lupus nephritis of III and IV class (according to WHO classification) have been treated with bindarit (600 mg) twice a day and with prednisone (5 mg twice or trice a day) for 8 weeks.

Before beginning treatment and at the end thereof UAE (Urinary Albumin Excretion) and interleukine-6 (IL-6) in urine have been measured.

At the end of the study; UAE levels were about 60% of the starting ones. In their turn, the urinary levels of IL-6 were about 10 picograms/ml also in those patients whose starting levels were 200 and 500 picograms/ml.

These results show that bindarit significantly reduces the severity of nephritis complications occuring in patients suffering from systemic lupus erythematosus treated with corticosteroids.

TABLE 1

Bindarit effect on the production of IL-6 induced by concanavaline A

| treatment | ng/ml | reduction (%) |
|---|---|---|
| concanavaline A | 16.5 + 6.4 | |
| bindarit | 10.2 + 2.1 | 38.2 |

TABLE 2

Effects on the median of survival

| treatment | average (days) | increase median (days) |
|---|---|---|
| control | 254 | |
| cyclophosphamide (22.5) | 259 | 4 |
| cyclophosphamide (45) | 294 | 40 |
| cyclophosphamide (90) | 330 | 76* |
| bindarit | 387 | 133* |
| bindarit + cyclophosphamide (22.5) | 408 | 154* |
| bindarit + cyclophosphamide (45) | 403 | 149* |

*p less than 0.001, Kaplan-Meier followed by LogRank test

TABLE 3

Effects on Tmax of proteinuria

| treatment | average (months) | p-value vs. controls* |
|---|---|---|
| control | 7 | |
| cyclophosphamide (22.5) | 8 | n.s. |
| cyclophosphamide (45) | 9 | 0.0018 |
| cyclophosphamide (90) | 10 | 0.00006 |
| bindarit | 9 | 0.0078 |
| bindarit + cyclophosphamide (22.5) | 9 | 0.0168 |
| bindarit + cyclophosphamide (45) | 10 | 0.00006 |

*Mann-Whitney test with corrections for multiple comparisons

1. U.S. Pat. No. 5,278,183.
2. Cioli V. et al. J. Rheumatol. 19: 1735–1742, 1992.

We claim:

1. A pharmaceutical composition comprising synergistic effective amounts of bindarit, an immunosuppressant and a pharmaceutically acceptable excipient.

2. A pharmaceutical composition according to claim 1, characterized in that said composition contains such an amount of immunosuppressant to insure an administration level of from 0.01 to 100 mg/Kg/day.

3. A composition according to claim 1 wherein the immunosuppressant comprises a corticosteroid.

4. A composition according to claim 1 wherein the immunosuppressant comprises prednisone.

5. A composition according to claim 1 wherein the immunosuppressant comprises a cyclophosphamide to insure an administration level of from 0.01 to 10 mg/kg/day.

6. A composition according to claim 1 wherein the immunosuppressant comprises prednisone in an amount to insure an administration level of from 0.01 to 1 mg/kg/day.

7. A pharmaceutical composition according to claim 1, wherein the immunosuppresant is selected from the group consisting of: cyclosporine, azatioprine, methotrexate, cyclophosphamide, FK 506, cortisolo, betametasone, cortisone, desametasone, flunisolide, prednisolone, methylprednisolone, prednisone, triamcinolone, alclometasone, amcinomide desonide and desoxymetasone.

8. A pharmaceutical composition according to claim 1 wherein said composition contains an amount of bindarit to insure an administration level of from 1 to 50 mg/Kg/day.

* * * * *